(12) United States Patent
Engelhard (10) Patent No.: US 8,017,073 B2
(45) Date of Patent: Sep. 13, 2011

(54) HIGH INTENSITY AIR PURIFIER (75) Inventor: Rolf Engelhard, Prescott, AZ (US)

(73) Assignee: Life Spring Limited Partnership, Las Vegas, NV (US)

( * ) Notice: Subject to any disclaimer, the term of this patent is extended or adjusted under 35 U.S.C. 154(b) by 0 days.

(21) Appl. No.: 12/628,180

(22) Filed: Nov. 30, 2009

(65) Prior Publication Data

US 2010/0143205 A1     Jun. 10, 2010

Related U.S. Application Data (60) Provisional application No. 61/200,375, filed on Nov. 28, 2008, provisional application No. 61/200,376, filed on Nov. 28, 2008.

(51) Int. Cl.
*A61L 2/08* (2006.01)
(52) U.S. Cl. ........................................... 422/24
(58) Field of Classification Search ........... 422/24
See application file for complete search history.

(56) References Cited

U.S. PATENT DOCUMENTS

| 2002/0098127 A1* | 7/2002 | Bollini | 422/121 |
| 2003/0230477 A1* | 12/2003 | Fink et al. | 204/157.3 |
| 2006/0057020 A1* | 3/2006 | Tufo | 422/24 |
| 2008/0112845 A1* | 5/2008 | Dunn et al. | 422/24 |

* cited by examiner

*Primary Examiner* — Robert J Warden
(74) *Attorney, Agent, or Firm* — Mintz, Levin, Cohn, Ferris, Glovsky & Popeo, PC (57) ABSTRACT

This document describes a high intensity air purifier (HAIP), a super oxidation purifier, and a controller for controlling operation of any of various purification systems. In some implementations, a HAIP includes an air purifier system coupled within a housing having an air inlet and an air outlet. The air purifier system includes a pre-filter coupled to the air inlet, an axial fan for receiving and forwarding air from the air inlet. The air purifier system further includes a UV reaction chamber having a UV-light source for providing UV light to the forwarded air from the air inlet and a reflective lining to reflect the provided UV light, to provide UV purified air from the UV reaction chamber. The air purifier system further includes a chemical catalyst cartridge for receiving the UV purified air from the UV reaction chamber, for further purifying the UV purified air, and a post filter coupled to the air outlet.

7 Claims, 9 Drawing Sheets

HIGH INTENSITY AIR PURIFIER

CROSS REFERENCE TO RELATED APPLICATIONS

This application claims the benefit of priority under 35 U.S.C. §119 to U.S. Provisional Patent Application Ser. No. 61/200,375, filed on Nov. 28, 2008, entitled, "Super oxidation air purifier" and U.S. Provisional Patent Application Ser. No. 61/200,376, filed on Nov. 28, 2008, entitled, "Advanced UV lamp controller", the entire disclosures of which is incorporated by reference herein.

BACKGROUND

Air quality is one of the most significant problems within homes and the workplace today. The modern environment is filled with impurities such as pollution and particulate matter, which makes its way into the air that occupies just about every structure. Some techniques for removing impurities include generating ions to bind to particulates and remove them from the general air. However, ionic air purifier systems generate excessive ozone, which can be harmful to occupants of a space being purified.

Accordingly, there is a need for an air purifier that does not rely on ion generation, but which is safe and harmless to human occupants of a space being purified.

SUMMARY

This document presents an air purifier system and method. In exemplary implementations, the system and method provides a surface that is coated with photo catalytic material, such as titanium dioxide, and includes an ultraviolet light source that irradiates the photo catalytic surface. The method includes bringing the air to be treated into contact with the photo catalytic surface, since only the air that touches the photo catalyst in a very thin boundary layer is purified.

In one aspect, a HAIP includes an air purifier system coupled within a housing having an air inlet and an air outlet. The air purifier system includes a pre-filter coupled to the air inlet, an axial fan for receiving and forwarding air from the air inlet. The air purifier system further includes a UV reaction chamber having a UV-light source for providing UV light to the forwarded air from the air inlet and a reflective lining to reflect the provided UV light, to provide UV purified air from the UV reaction chamber. The air purifier system further includes a chemical catalyst cartridge for receiving the UV purified air from the UV reaction chamber, for further purifying the UV purified air, and a post filter coupled to the air outlet. The housing can be attached to a rotating AC plug for convenient attachment to a standard wall electrical outlet. The housing can be shaped as a tube or cylinder, and have a small form factor for easy and unobtrusive deployment within a house or workspace.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

This document describes a high intensity air purifier (HAIP), a super oxidation purifier, and a controller for controlling operation of any of various purification systems described herein.

In general, a HAIP includes an axial fan, an inlet radial louver, a reaction chamber having a UV light source, an outlet radial louver, and a photo catalyst. The axial fan moves air into and through the reaction chamber, not in a linear, but in a spiral fashion. This is due to the rotation of the fan's impeller blades. The spiral airflow around the UV light source is desirable because it creates more even exposure of all air to UV light, and it promotes spinning of the airborne particles, which gives UV exposure to all sides of the particles.

Immediately after leaving the axial fan, the moving air has to pass through the inlet radial louver. The louver blades are angled such that they further promote the spiral airflow created by the axial fan. The surface of the radial louver that is facing inward, toward the UV reaction chamber, is coated with the photo catalyst. This surface is heavily irradiated with ultraviolet light. First, the UV light comes directly from a UV lamp that is positioned perpendicular to the radial louver. Second, the UV light comes from the walls of the UV reaction chamber, which are lined with a reflective lining. The reflective lining is a "lambertian" reflector that reflects light in all directions, thereby striking the photo catalyst from all angles with massive amounts of UV.

As with the radial louver on the inlet of the UV reaction chamber, the second radial louver is located on the outlet side of the UV chamber. The second radial louver functions in the same way, and can also be coated with photo catalyst material. The second radial louver further promotes spiral flow of the air. The placement of the radial louver photo catalysts, in combination with the lambertian reflective lining of the UV reaction chamber, creates a "light tight" chamber from which no UV energy can escape unused. Radially, no UV light escapes because it is continually being reflected inward to increase the UV intensity within the chamber. Longitudinally traveling light, which would otherwise escape from the ends of the UV reaction chamber, strikes the photo catalytic surfaces on both ends where the resulting chemical reaction destroys microbial and chemical contaminants. This "light tight" construction also serves to prevent human eyes and skin from becoming exposed to harmful UV light.

One further advantage of this construction is that the radial louver in combination with the axial fan creates a turbulent airflow over the photo catalytic surfaces. Since the photo catalytic reaction only occurs directly on the photo catalyst surface, it is beneficial to create a turbulent airflow that brings all the air to this surface for a short contact period.

The outlet side of the UV reaction chamber can also house a chemical catalyst. This catalyst interacts with ozone and carbon monoxide to convert them to oxygen and carbon dioxide (among other reactions). The chemical catalytic reaction only takes place where the air touches the catalytic surfaces. Again, it is desirable to have a turbulent flow in the chemical catalyst. This is also achieved by the radial louvers, yet another advantage of this arrangement. The HAIP can be housed within a housing, which in turn can be attached to a rotating AC plug for convenient attachment to a standard wall electrical outlet. The housing can be shaped as a tube or cylinder, and have a small form factor for easy and unobtrusive deployment within a house or workspace.

High Intensity Air Purifier (HAIP)

Figure 1:
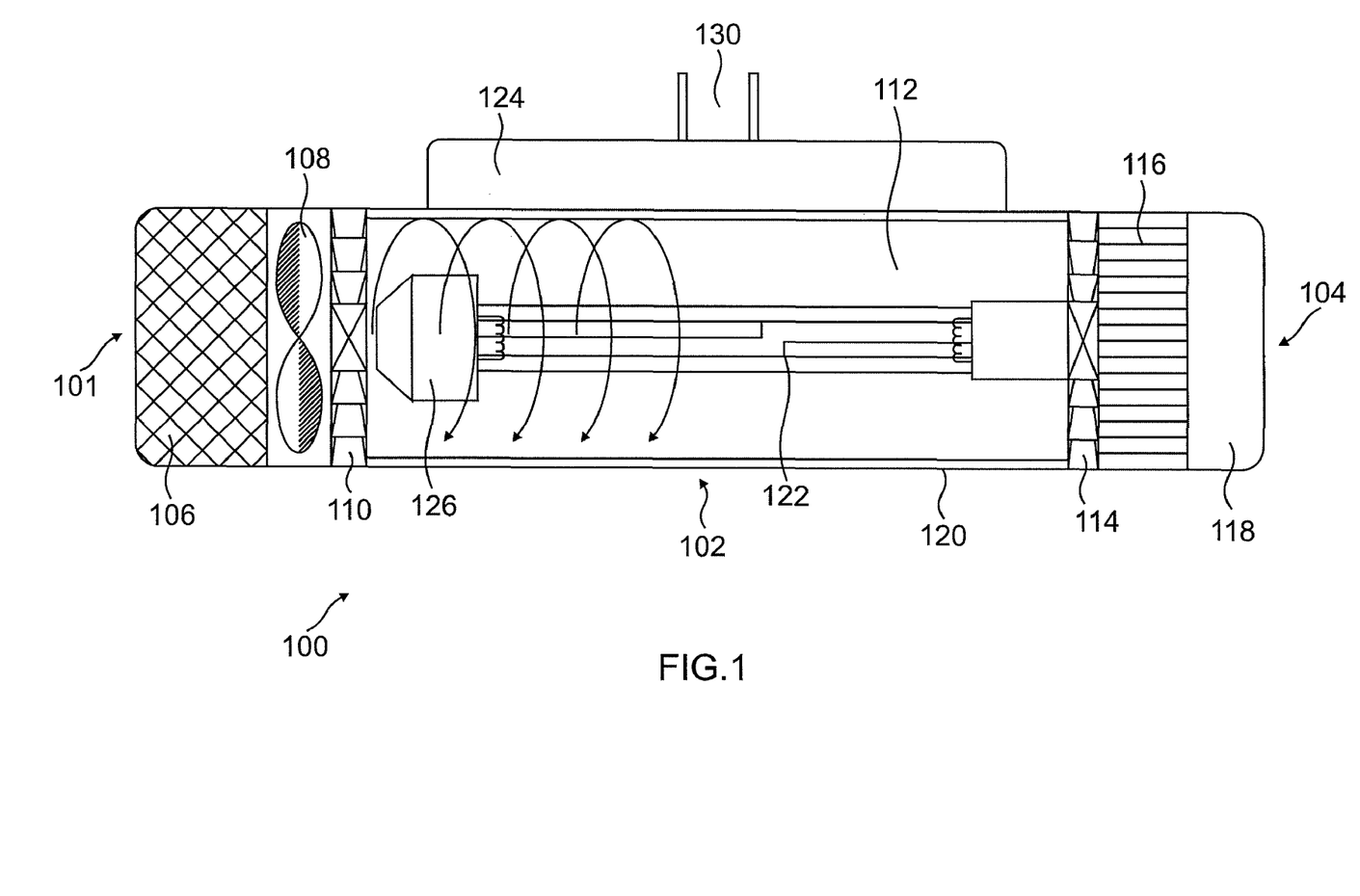
FIG. 1 is a cut-away view of a high intensity air purifier in accordance with preferred implementations.
Figure 2:
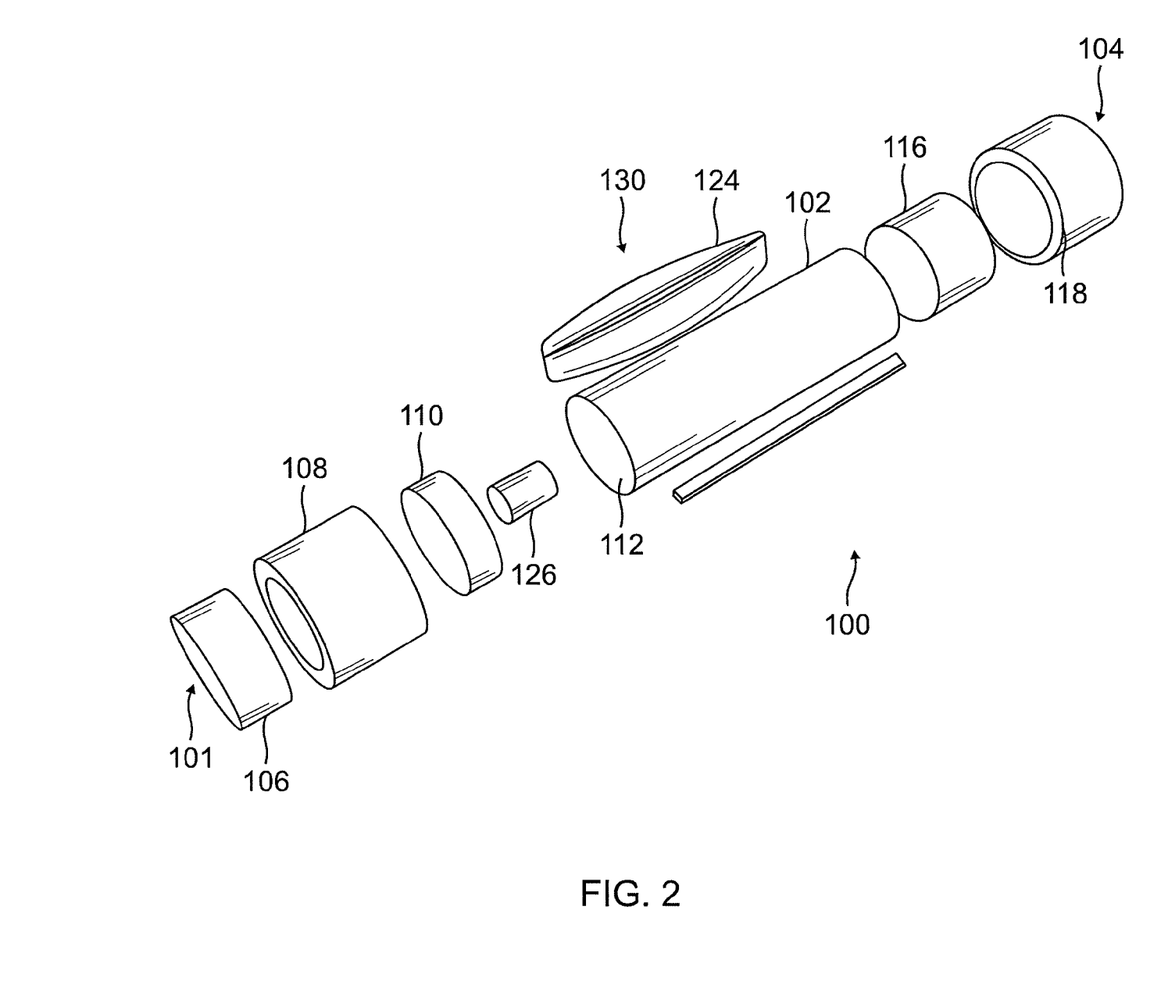
FIG. 2 is an exploded view of a high intensity air purifier in accordance with preferred implementations.

FIGS. 1 and 2 show a cross sectional view and an exploded view, respectively, of a HAIP 100 that is preferably formed and configured to be plugged directly into a standard two- or three-pronged electrical outlet for immediate and continuous operation. The HAIP 100 can rotate relative to the electrical outlet to change a direction in which it takes in air and discharges purified air. For instance, an inlet 102 of the HAIP 100 can be directed toward a source of air contamination such as a pet food dish, pet bed or litter box, or waste basket. In this way, a relative low pressure area is created around the inlet 102, which draws in contaminated air away from the source of air contamination, where it is treated within the HAIP 100 to reduce or eliminate particulates, odors, bacteria, viruses, etc., and the HAIP 100 in turn discharges purified air through an outlet 104 toward an area where clean, treated air is desirable.

Figure 6:
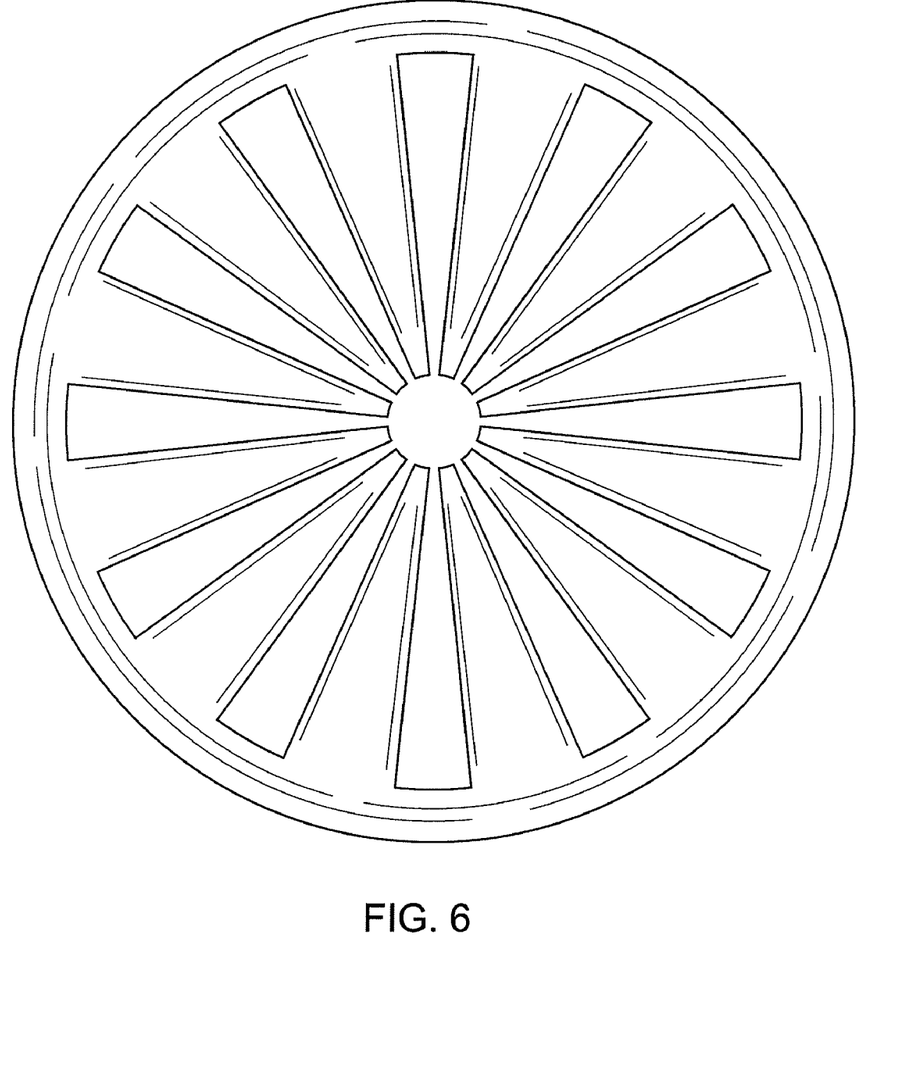
FIG. 6 illustrates radial louvers that inhibit UV light from exiting the chamber.

In accordance with some implementations, the HAIP 100 includes a pre-filter 106 connected with the inlet 102, and an axial fan 108 for drawing in air into the inlet 102 and pre-filter 106, and toward a first radial louver 110, an example of which is shown in FIG. 6. The first radial louver 110 is connected to an input to a reaction chamber (RC) 112, which is part of an ultraviolet-based super oxidation purifier (SOP) system explained in more detail below. The axial fan 108 and first radial louver 110 provide a spiral airflow within the HAIP 100, while also preventing a direct line of sight into the RC 112 to prevent human exposure to harmful UV rays.

The pre-filter 106 reduces relatively larger particulates and other air contaminants from the air drawn into the inlet 102 before the air reaches the RC 112. The pre-filter 106 is preferably selectable and configurable for a particular particulate or contaminant. For example, the pre-filter 106 can include a smoke filter, for areas where smoke is present from sources such as tobacco products, wood stoves, outside environment (brush fires, etc.) or other smoke sources. The pre-filter 106 can include a pet filter, for areas where pet hair, feathers, dander, etc., are present. In yet other implementations, the pre-filter 106 can include a dust and pollen filter, for areas having high pollen and/or dust contamination. The pre-filter 106 can be configured as one or more replaceable cartridges, for addressing a particular life of each cartridge before it needs to be replaced. The pre-filter 106 can be formed of a cleanable cartridge, such as made of a sponge-like material. In yet other implementations, the pre-filter 106 is configured as a static filter which attracts particulates by electrostatic energy. These types of static filters can be routinely cleaned by flushing or vacuuming.

The HAIP 100 further includes a second radial louver 114 connected to an output of the RC 112, a catalyst cartridge 116 connected to the second radial louver 114, and a post filter 118 connected to the catalyst cartridge 116 and which at least partly forms the outlet 104 of the HAIP 100. The post filter 118 can include an aroma cartridge that attaches proximate to the outlet 104 and which is configured to release an aroma into the purified air being discharged through the outlet 104. The aroma cartridges are replaceable, and can include any of a variety of scents, such as pine, gardenia, menthol, vanilla, etc. Each aroma cartridge will preferably have a finite life, after which it will need to be replaced.

Super Oxidation Purifier (SOP)

The SOP combines a number of technologies to most effectively destroy various contaminants in various gases and liquids, such as air and water, as described further below.

Reaction Chamber (RC)

The RC 112 houses an ultraviolet (UV) light source, which can also produce ozone, as well as contains a coating that keeps maximum UV light within the UV-C range and to minimize loss of UV light to non-reflective surfaces. The RC 112 also prevents UV light from escaping from the HAIP 100, and is constructed to make impossible human exposure to the UV light. The RC 112 is also designed to allow maximum airflow with minimal friction loss. In a preferred exemplary implementation, the air is pushed by the UV light source in a spiral fashion, which will allow the most even and consistent exposure of all air particles to the UV light. This spiral airflow can be achieved by cooperation between the axial fan 108 and first radial louver 110 at the inlet to the RC 112. The axial fan 108 moves the air in a spiral fashion with the rotation of fan's impeller, and the first radial louver 110 deflects the air as it passes the axial fan 108.

Figure 8:
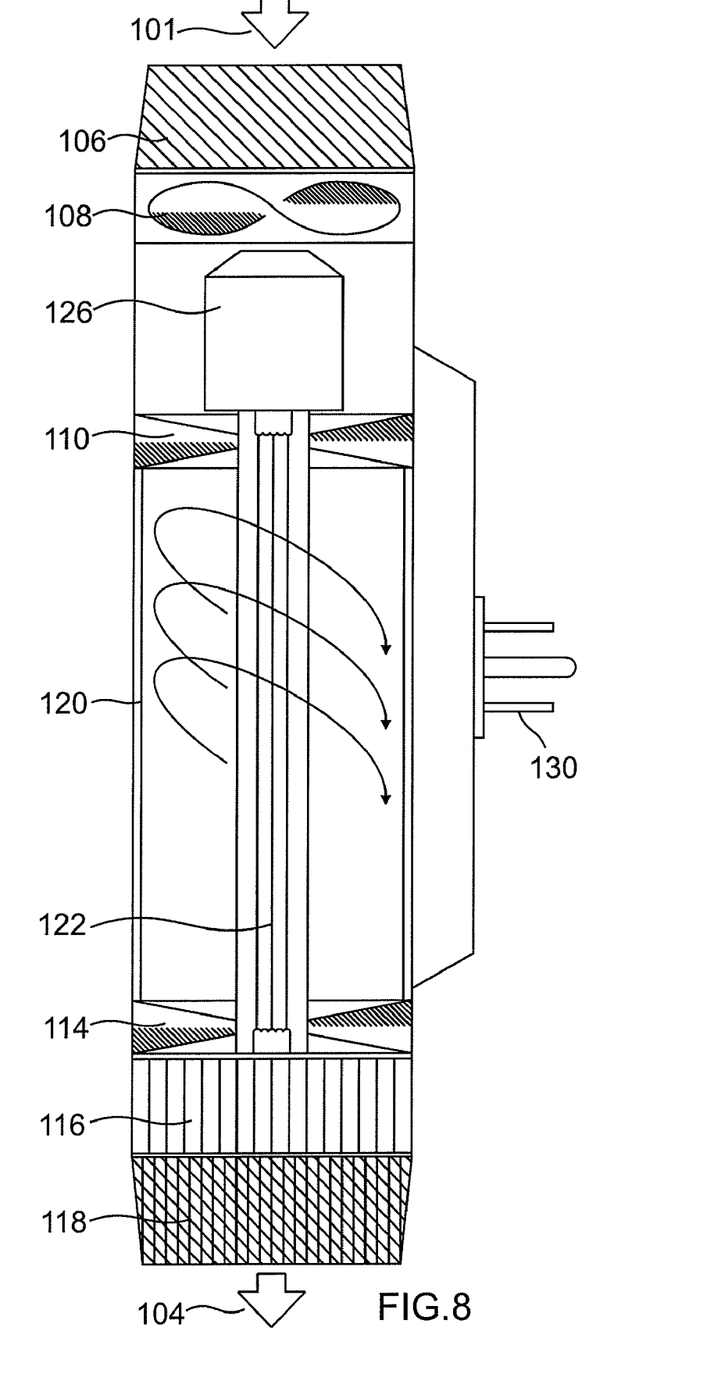
FIG. 8 is a cut-away view of a high intensity air purifier in accordance with an alternative implementation.

In some implementations, as shown in FIG. 8, the UV lamp ballast 126 can be arranged after the axial fan 108 and before the inlet radial louver 110, for shielding of UV light from the UV light source 122, and so as to not create a spiral forward air flow until just at the UV light source 112. Also, this arrangement allows air to cross over and cool the UV lamp ballast in a laminar flow, rather than a spiral flow.

The RC 112 is formed by at least part of the purifier housing 102, which at least part is lined with a reflective material 120 that is highly reflective to UV light, particularly in the UV-C range, and in some preferred implementations specifically in the 185 and 254 nanometer ranges. In one preferred implementation, the reflective material 120 is a "lambertian" reflector, also known as a diffused reflector, that reflects light at all angles to expose all air and contaminant molecules from all sides. Because of this high efficiency reflector, the HAIP 100 can achieve high UV intensities in a smaller chamber than would otherwise be required in a conventional chamber.

Figure 3:
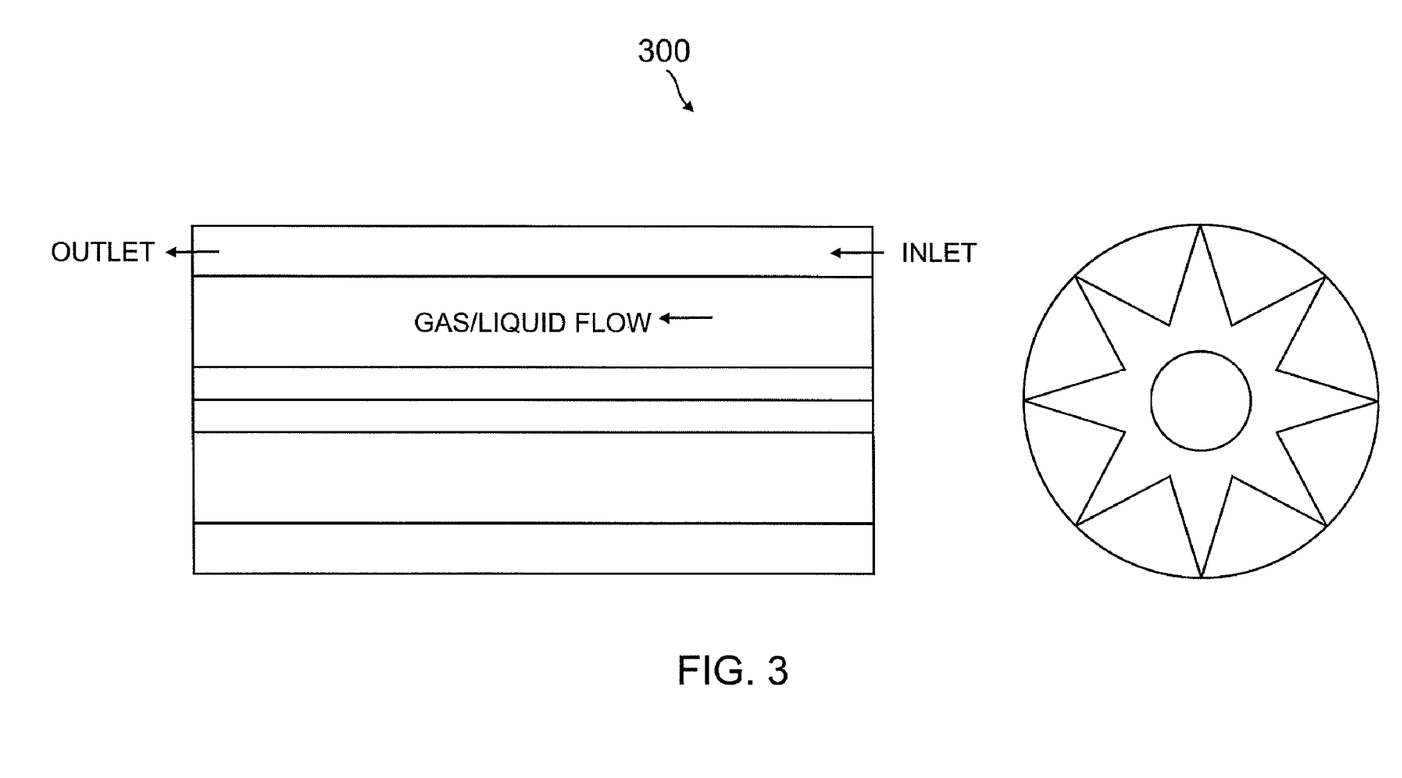
FIG. 3 shows a star pattern chamber.
Figure 4A:
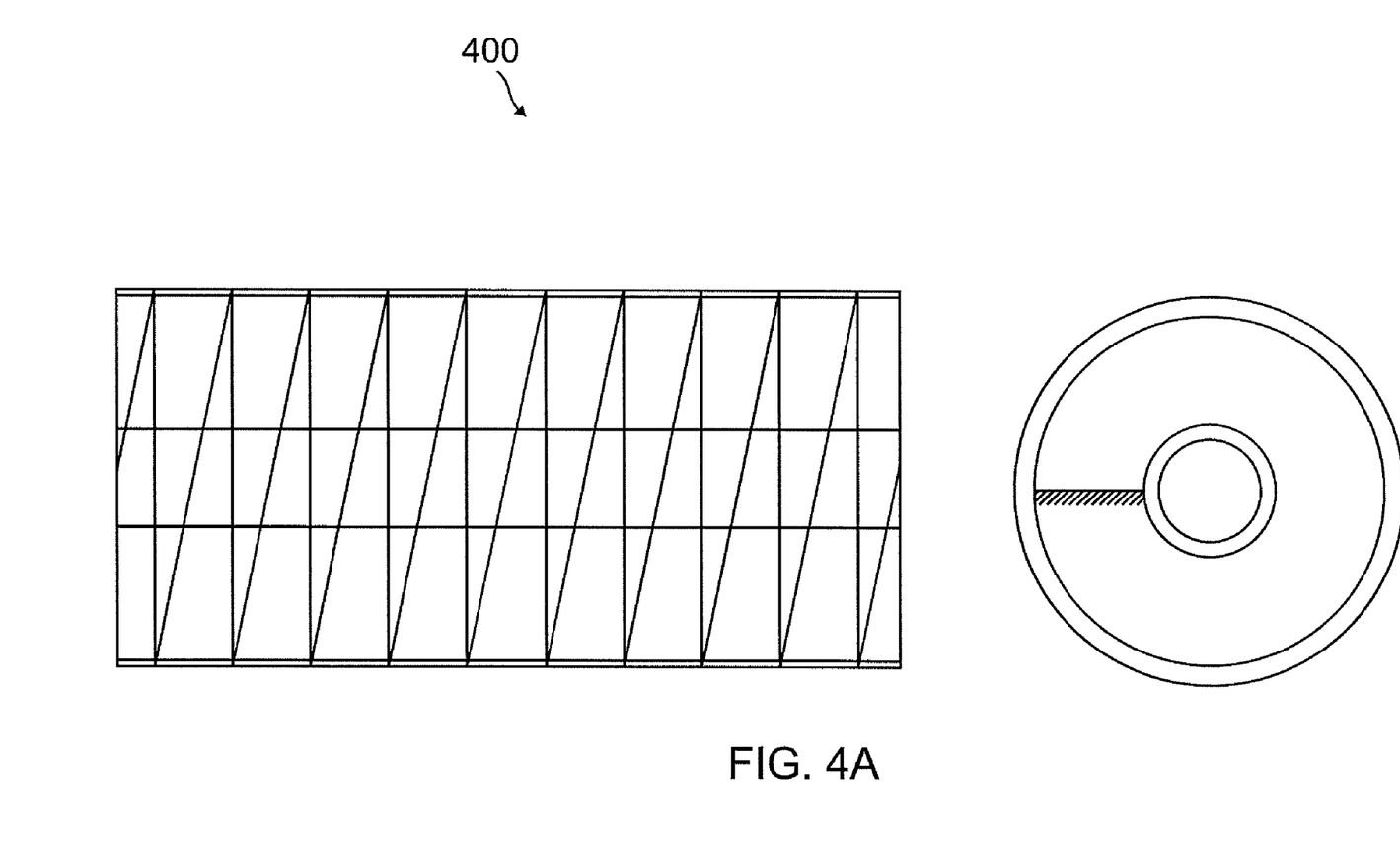
FIGS. 4A and 4B show a continuous helical ramp chamber.
Figure 4B:
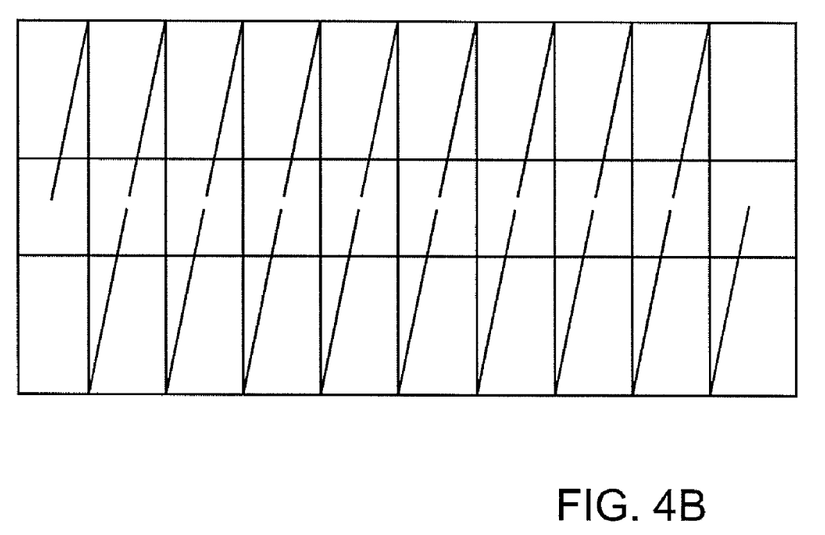
Figure 5:
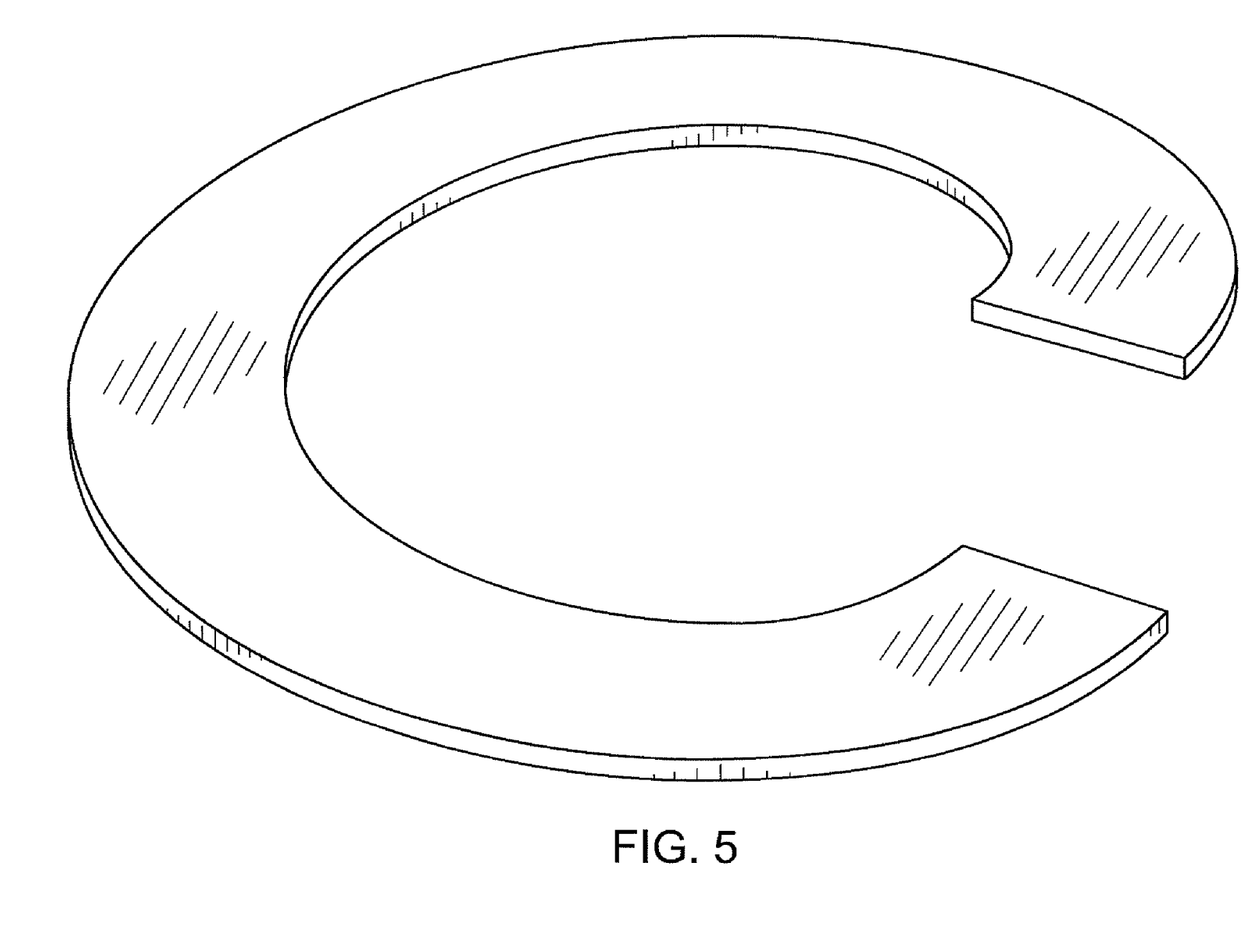
FIG. 5 shows a modular ramp chamber.

The RC 112 housing can be constructed of metal, glass, ceramic, plastic, or the like, and coated with $TiO_2$ on the inside surface. The RC 112 is formed to a shape or pattern maximize a surface area. FIG. 3 shows a star pattern chamber 300, which has a number of angled peaks and valleys formed linearly along the length of the chamber and RC 112 housing. FIGS. 4A and 4B show a continuous helical ramp chamber 400. FIG. 5 shows a modular ramp chamber 500.

The RC 112 includes a UV light source 122, which can either be ozone producing or non-ozone producing. The UV light source 122 is preferably a low pressure mercury vapor lamp. In the ozone producing implementation, the light source 122 produces light in the 254 nm (germicidal) range and in the 185 nm (ozone producing) range. The interaction between the two different wavelength ranges generates hydroxyl radicals, which are very powerful oxidizers that destroy many microbiological and chemical compounds. In the non-ozone producing implementation, the light source 122 produces light primarily in the 254 nm (germicidal) range, which can destroy microorganisms such as viruses, bacteria, mold spores, parasites, etc. The UV light source 122 is mounted in the RC 112 such that it will not function should any attempt be made to remove it from the chamber.

The optional catalyst cartridge 116 attaches to the outlet of the RC 112, and is configured to convert ozone to oxygen. The capacity of the catalyst is preferably matched to the ozone production of the UV lamp to reduce ozone emissions from the HAIP 100 to desirable levels. The catalyst cartridge 116 can be constructed of an aluminum or ceramic substrate that is coated with a catalytic material, such as manganese dioxide, for instance.

Photo-Catalysis is defined as "acceleration by the presence of a catalyst". A catalyst does not change in itself or being consumed in the chemical reaction. This definition includes photosensitization, a process by which a photochemical alteration occurs in one molecular entity as a result of initial absorption of radiation by another molecular entity called the photosensitized. Chlorophyll of plants is a type of photo catalyst. Photo catalysis compared to photosynthesis, in which chlorophyll captures sunlight to turn water and carbon dioxide into oxygen and glucose, photo catalysis creates strong oxidation agent to breakdown any organic matter to carbon dioxide and water in the presence of photo catalyst, light and water.

Mechanism of Photo-Catalysis

When photo catalyst titanium dioxide ($T_1O_2$) absorbs Ultraviolet (UV) radiation from sunlight or illuminated light source (fluorescent lamps), it will produce pairs of electrons and holes. The electron of the valence band of titanium dioxide becomes excited when illuminated by light. The excess energy of this excited electron promoted the electron to the conduction band of titanium dioxide therefore creating the negative-electron (e−) and positive-hole (h+) pair. This stage is referred as the semiconductor's 'photo-excitation' state. The energy difference between the valence band and conduction band is known as the 'Band Gap'. Wavelength of the light necessary for photo-excitation is: 1240 (Planck's constant, h)/3.2 ev (band gap energy)=388 nm.

Sterilizing Effect

Photo catalyst does not only kill bacteria cells, but also decompose the cell itself. The titanium dioxide photo catalyst has been found to be more effective than any other antibacterial agent, because the photo catalytic reaction works even when there are cells covering the surface and while the bacteria are actively propagating. The end toxin produced at the death of cell is also expected to be decomposed by the photo catalytic action. Titanium dioxide does not deteriorate and it shows a long-term anti-bacterial effect. Generally speaking, disinfections by titanium oxide are three times stronger than chlorine, and 1.5 times stronger than ozone.

Deodorizing Effect

On the deodorizing application, the hydroxyl radicals accelerate the breakdown of any Volatile Organic Compounds or VOCs by destroying the molecular bonds. This will help combine the organic gases to form a single molecule that is no harmful to humans thus enhance the air cleaning efficiency. Some of the examples of odor molecules are: Tobacco odor, formaldehyde, nitrogen dioxide, urine and fecal odor, gasoline, and many other hydrocarbon molecules in the atmosphere. Air purifier with T102 can prevent smoke and soil, pollen, bacteria, virus and harmful gas as well as seize the free bacteria in the air by filtering percentage of 99.9% with the help of the highly oxidizing effect of photo catalyst (T102).

Air Purifying Effect

The photo catalytic reactivity of titanium oxides can be applied for the reduction or elimination of polluted compounds in air such as NOx, cigarette smoke, as well as volatile compounds arising from various construction materials. Also, high photo catalytic reactivity can be applied to protect lamp-houses and walls in tunneling, as well as to prevent white tents from becoming sooty and dark. Atmospheric constituents such as chlorofluorocarbons (CFCs) and CFC substitutes, greenhouse gases, and nitrogenous and sulfurous compounds undergo photochemical reactions either directly or indirectly in the presence of sunlight. In a polluted area, these pollutants can eventually be removed.

Water Purification

Photo catalyst coupled with UV lights can oxidize organic pollutants into nontoxic materials, such as CO2 and water and can disinfect certain bacteria. This technology is very effective at removing further hazardous organic compounds (TOCs) and at killing a variety of bacteria and some viruses in the secondary wastewater treatment. Pilot projects demonstrated that photo catalytic detoxification systems could effectively kill fecal coli form bacteria in secondary wastewater treatment.

Controller

An electronic housing 124 houses an electronic control module and controller circuit. The electronic control module includes a lamp ballast 126. The lamp ballast 126 can be an alternating current (AC) ballast that plugs directly into a household electrical outlet for typical 100-240 VAC. Alternatively, the lamp ballast 126 can be a direct current (DC) ballast that will typically work on 12 VDC. The DC ballast version of the HAIP 100 is designed for desktop units, portable units, automotive, recreational vehicle, and boat use, as just some examples. The DC ballast is described further below. In yet another alternative, the lamp ballast 126 can be a universal serial bus (USB) powered ballast, which can be connected to a USB port of a laptop or desktop computer to provide a user with clean air.

The electronic control module incorporates the axial fan 108 that moves air through the various air purification components within the unit, as described above. In some implementations, the axial fan 108 is variable speed. On a high-speed setting, the axial fan 108 moves more air through the air purifier for greater efficiency, but will also generate more noise. A low-speed setting may be preferred for a quiet room such as a bedroom or for night use. In some implementations, the HAIP 100 can include a manual controller for controlling the fan speed. In other implementations, the HAIP 100 can include an automatic mode, by which fan speed can be controlled by a light sensor. For example, the HAIP 100 can be run on a "nighttime/quiet mode" that will run the axial fan 108 at low speed during the night, or the HAIP 100 can be run on a "daytime/quiet mode" that will run the axial fan 108 at low speed during the day.

The HAIP 100 can also include a light or series of lights incorporated into the housing 102 that indicate operation of the device. The lights can be programmed to gently pulsate or wave during normal operation. Optionally, a light or lights can be set to operate as a nightlight. The light sensor can be used to activate the nightlight light or lights during darkness.

Figure 7:
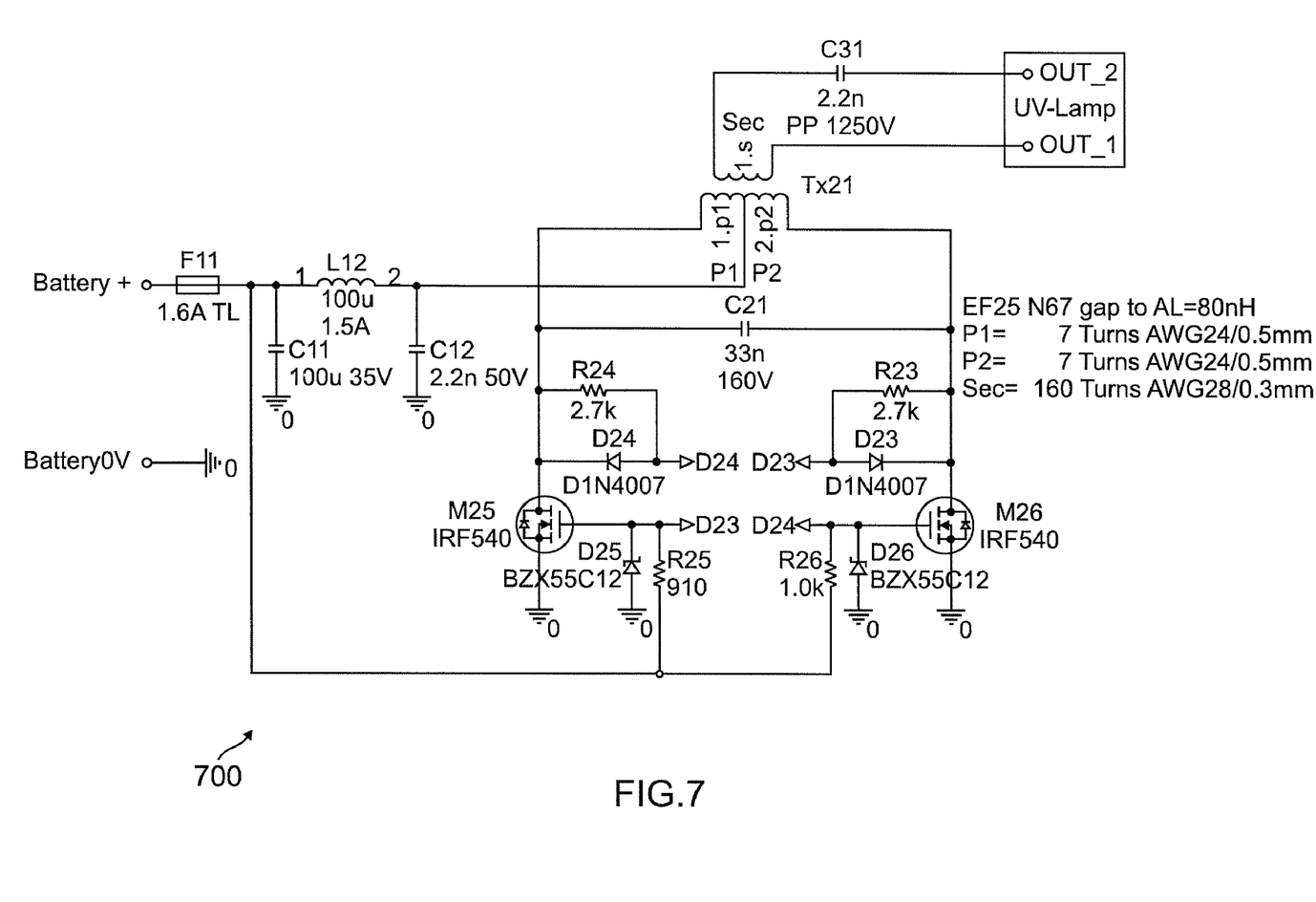
FIG. 7 illustrates a controller circuit for controlling a device such as an air purifier as disclosed herein.

FIG. 7 is a circuit diagram of a circuit 700 for a DC lamp ballast. The circuit 700 is structured to provide starting voltage and operation current to drive a special fluorescent lamp, and is built to be rugged, simple, and cost effective. The circuit 700 includes a number of MOSFETs used as power switches, with no special driver integrated circuits. Accordingly, there are very low losses due to low on-resistance and drive requirements.

The circuit 700 operates at a high operation frequency, and feedback is arranged as in Astable Multi Vibrators (AMVs) from drain to the gate. Thus, no driver winding on the transformer required, which provides physical stability in case of lamp failure since driving power is independent of the transformer state. Due to the lack of small signal gain in this configuration, supply voltage has to be switched on very fast (mechanically) to prevent each MOSFET from simply conducting and heating to destruction.

In order to keep switching and gate driving losses low, this circuit takes advantage of the stored charge in the "slow" feedback diodes. Thus, the circuit 700 achieves very low DC driving losses and high speed switching as the stored charge in the diode junction is transferred to the gate capacitance with the full drain current as fast as drain rises. This type of oscillator uses a transformer (TX21) in resonance (with C21, and C31 with load connected) to provide the desired output voltage and power.

This circuit 300 is current driven, and inductor L12 provides a low ripple current to the center of the transformer. AC characteristics of L12 are of minor importance due to the low ripple current. Transistor switching occurs at nearly zero voltage, so there has to be only a low margin in breakdown voltage. Instead of a third driving winding and BJT as power switches, diodes D23, D24 drive the gates of MOSFETs M25, M26 to form an Astable Multi Vibrator (AVM). The resistors R25 and R26 feed some current to the diodes D23, D24. They provide the stored charge in the diodes required for driving the gates very rapidly. Therefore, the use of "slow diodes" driving the gates with the drain current helps achieve low power fast switching of the MOSFETs.

Zener diodes D25, D26 dissipate the surplus charge in the feedback diodes to prevent gate breakdown (20V) and destruction of the MOSFETs. This topology is very rugged to supply- or load related problems. Primary inductance of transformer TX21 and C21 determine the resonance frequency in case of no load (lamp failure) and prevents destruction due to transformer heating. In order to achieve low current ripple in the primary, the no-load frequency has been found to be an odd harmonic (i.e., about three times in this design) of the operating frequency with load.

With load connected, secondary inductance and C31 form the main resonance. C31 has to withstand the full output swing and transients (>1000V) and, for the high reactive power stored in the transformer, it has to be low loss, and is preferably made of polypropylene. Resistors R23, R24, in parallel to diodes D23, D24, add some linear small signal feedback to the diodes' feedback. While rising, power supply voltage passes a region (3-4V) of sufficient small signal gain to start the oscillator at moderate supply current (<0.5 A). Once started, oscillation amplitude rises and the diodes D23, D24 override R23, R24 and speed up feedback by stored charge.

Although a few embodiments have been described in detail above, other modifications are possible. For instance, the inlet 102 and/or outlet 104 of the HAIP 100 can include a directionally changeable nozzle or some other dynamically adjustable device for providing a wider range of inlet and outlet directionality. Other embodiments may be within the scope of the following claims.

The invention claimed is:

1. An air purifier apparatus comprising:
   a housing rotatably coupled with an AC plug, the housing having an air inlet for receiving unclean air and an air outlet for providing purified air;
   an air purifier system coupled within the housing, the air purifier system comprising:
      a pre-filter coupled to the air inlet;
      an axial fan for receiving and forwarding air from the air inlet in a spiral flow;
      a first radial louver for further promoting the spiral flow of the air and providing the spiral flow of the air around a UV light in a UV reaction chamber,
      the UV-light source providing UV light to the spiral flow of the air from the first radial louver and having a reflective lining to reflect the UV light, the UV reaction chamber to provide UV purified air from the UV reaction chamber;
      a chemical catalyst cartridge for receiving the UV purified air from the UV reaction chamber, for further purifying the UV purified air with a chemical catalyst; and
      a post filter coupled to the air outlet to output purified, filtered air.

2. The air purifier apparatus in accordance with claim 1, wherein the chemical catalyst cartridge includes a photo catalyst substance.

3. The air purifier apparatus in accordance with claim 2, wherein the photo catalyst substance includes titanium dioxide.

4. The air purifier apparatus in accordance with claim 1, wherein the UV light source includes a low pressure mercury vapor lamp.

5. The air purifier apparatus in accordance with claim 1, wherein the reflective lining is a lambertian reflector that reflects light in all directions.

6. The air purifier apparatus in accordance with claim 1, wherein the first radial louver includes a plurality of angled blades, each of the angled blades having an outer surface facing the axial fan to block the UV light from escaping the UV reaction chamber through the first radial louver, and an inner surface coated with a photo catalyst and facing the UV reaction chamber.

7. The air purifier apparatus in accordance with claim 6, further comprising a second radial louver for receiving the spiral flow of the air from the UV reaction chamber and providing the spiral flow of air to the chemical catalyst cartridge.

* * * * *